US009861341B2

(12) United States Patent
Kawagishi et al.

(10) Patent No.: US 9,861,341 B2
(45) Date of Patent: Jan. 9, 2018

(54) ULTRASOUND DIAGNOSIS APPARATUS

(71) Applicant: Toshiba Medical Systems Corporation, Otawara-shi (JP)

(72) Inventors: Tetsuya Kawagishi, Nasushiobara (JP); Akihiro Kakee, Nasushiobara (JP); Kuramitsu Nishihara, Otawara (JP); Hiroki Yoshiara, Nasushiobara (JP); Atsushi Sumi, Otawara (JP); Yasuyuki Masakari, Nasushiobara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 0 days.

(21) Appl. No.: 14/167,170

(22) Filed: Jan. 29, 2014

(65) Prior Publication Data
US 2015/0209006 A1 Jul. 30, 2015

(51) Int. Cl.
A61B 8/00 (2006.01)
A61B 8/08 (2006.01)

(52) U.S. Cl.
CPC .......... *A61B 8/5207* (2013.01); *A61B 8/4416* (2013.01); *A61B 8/54* (2013.01); *A61B 8/4245* (2013.01); *A61B 8/463* (2013.01)

(58) Field of Classification Search
USPC ....................................................... 600/440
See application file for complete search history.

(56) References Cited

U.S. PATENT DOCUMENTS

| 4,463,763 A | * | 8/1984 | Koyano et al. | 600/440 |
| 4,735,211 A | * | 4/1988 | Takasugi | 600/443 |
| 4,972,838 A | * | 11/1990 | Yamazaki | 600/455 |

(Continued)

FOREIGN PATENT DOCUMENTS

| JP | 62-179443 A | 8/1987 |
| JP | 5-137716 | 6/1993 |

(Continued)

OTHER PUBLICATIONS

Office Action dated May 12, 2015 in Japanese Patent Application No. 2011-196110.

(Continued)

*Primary Examiner* — Joel F Brutus
(74) *Attorney, Agent, or Firm* — Oblon, McClelland, Maier & Neustadt, L.L.P.

(57) ABSTRACT

An ultrasound diagnosis apparatus includes a transmission and reception unit, an addition unit, an image generation unit, and a control unit. The transmission and reception unit performs a set of ultrasound transmission and reception in a first mode or a plurality of sets of ultrasound transmission and reception in a second mode along the same scan line. Each set of ultrasound transmission and reception is constituted of repeated ultrasound transmission and reception sequentially performed in reversed phase polarity along the same scan line. The addition unit adds reflected wave data in the second mode. The image generation unit generates an image by using reflected wave data in the first mode or in the second mode. The control unit switches the first mode and the second mode. The transmission and reception unit performs a set or a plurality of sets of ultrasound transmission and reception according to a switching operation.

16 Claims, 11 Drawing Sheets

(56) References Cited

U.S. PATENT DOCUMENTS

| | | | | |
|---|---|---|---|---|
| 5,724,976 | A | * | 3/1998 | Mine et al. .................. 600/459 |
| 6,104,670 | A | * | 8/2000 | Hossack ............ G01N 29/2456 367/11 |
| 6,436,046 | B1 | * | 8/2002 | Napolitano ......... G01S 7/52039 600/447 |
| 2004/0133106 | A1 | * | 7/2004 | Kakee et al. ................ 600/437 |
| 2012/0130248 | A1 | * | 5/2012 | Fatemi .................... A61B 8/06 600/454 |

FOREIGN PATENT DOCUMENTS

| | | |
|---|---|---|
| JP | 6-61211 U | 8/1994 |
| JP | 7-213524 A | 8/1995 |
| JP | 10-118068 | 5/1998 |
| JP | 11-89846 | 4/1999 |
| JP | 2002-34985 | 2/2002 |
| JP | 2002-143158 | 5/2002 |
| JP | 2002-165796 | 6/2002 |
| JP | 2003-52698 | 2/2003 |
| JP | 2014-181209 | 7/2004 |
| JP | 2005-270317 | 10/2005 |
| JP | 2008-178470 A | 8/2008 |
| JP | 2009-45285 A | 3/2009 |
| JP | 2010-22817 | 2/2010 |
| JP | 2013-056033 A | 3/2013 |
| WO | WO 2010/055879 | 5/2010 |

OTHER PUBLICATIONS

Office Action dated Dec. 8, 2015 in Japanese Application No. 2011-196110.

International Search Report dated Mar. 11, 2014 in PCT/JP2014/052943.

Office Action dated Mar. 22, 2016 in Japanese Application No. 2011-196110.

* cited by examiner

ULTRASOUND DIAGNOSIS APPARATUS

FIELD

Embodiments described herein relate generally to an ultrasound diagnosis apparatus.

BACKGROUND

An ultrasound diagnosis apparatus transmits ultrasonic beams to a biological body and receives resulting reflected waves to apply the principle of pulse reflection to the resulting reflected waves thus received, thereby generating an image of biological tissues. The ultrasound diagnosis apparatus has characteristics such as non-invasive, small size, and real-time display and is widely used in medical fields.

In general, sensitivity in a deep portion of the body tends to decrease in medical examinations using the ultrasound diagnosis apparatus. In order to increase the sensitivity in a deep portion of the body, for example, decreasing the frequencies of ultrasonic pulses may be considered, but that also decreases spatial resolution. It may also be considered, for example, to stop using a mode in which harmonic components are visualized (hereinafter referred to as "harmonic imaging mode") and to start using a normal mode in which the fundamental is visualized, but that does not provide an advantage of reducing artifacts, although the reduction in artifacts is expected in the harmonic imaging mode. As yet another example, increasing acoustic pressure may be considered, but it is difficult to significantly increase the acoustic pressure because of a limitation of mechanical index (MI). When the ultrasound diagnosis apparatus performs contrast imaging, it can increase the acoustic pressure to some extent, but that leads to bubble destruction, whereby the opposite effect may occur such as insufficiently enhanced contrast image. Thus, none of the measures described above can appropriately increase sensitivity in a deep portion of the body.

DETAILED DESCRIPTION

The following describes an ultrasound diagnosis apparatus according to embodiments.

The ultrasound diagnosis apparatus according to the embodiments includes a transmission and reception unit, an addition unit, an image generation unit, and a control unit. The transmission and reception unit performs a set or a plurality of sets of ultrasound transmission and reception along the same scan line, each set of which is constituted of repeated ultrasound transmission and reception sequentially performed in reversed phase polarity along the same scan line. The addition unit adds reflected wave data received from a plurality of sets of ultrasound transmission and reception performed by the transmission and reception unit. The image generation unit generates an image by using reflected wave data of a set of ultrasound transmission and reception, or using the reflected wave data of a plurality of sets of ultrasound transmission and reception added by the addition unit. The control unit switches a first mode in which a set of ultrasound transmission and reception is performed, and a second mode in which a plurality of sets of ultrasound transmission and reception are performed. The transmission and reception unit performs a set or a plurality of sets of ultrasound transmission and reception in accordance with a switching operation by the control unit.

First Embodiment

Figure 1:
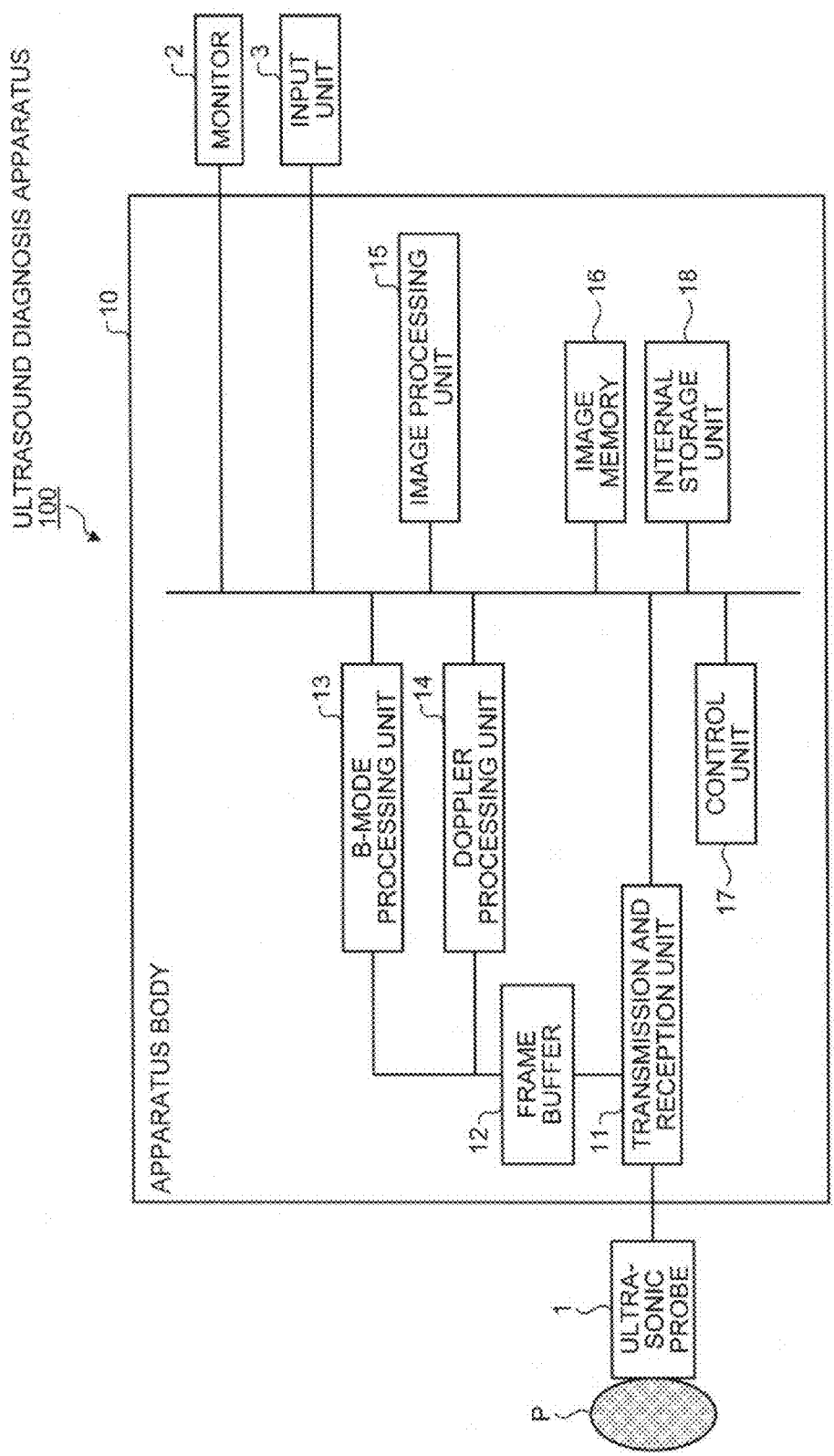
FIG. 1 is a diagram for explaining a configuration of an ultrasound diagnosis apparatus according to a first embodiment.

A first embodiment is described. FIG. 1 is a diagram for explaining a configuration of an ultrasound diagnosis apparatus 100 according to the first embodiment. As illustrated in FIG. 1, the ultrasound diagnosis apparatus 100 according to the first embodiment includes an ultrasonic probe 1, a monitor 2, an input unit 3, and an apparatus body 10.

The ultrasonic probe 1 includes a plurality of piezoelectric transducer elements. The piezoelectric transducer elements generate ultrasound pulses based on a drive signal supplied from a transmission and reception unit 11 included in the apparatus body 10 to be described later, and receive reflected waves from a subject P to convert the reflected waves thus received into electric signals. The ultrasonic probe 1 also includes a matching layer provided to the piezoelectric transducer elements and backing material preventing ultrasonic waves from traveling behind the piezoelectric transducer elements.

When ultrasound pulses are transmitted from the ultrasonic probe 1 to the subject P, the ultrasonic pulses thus transmitted are sequentially reflected from the planes of discontinuity of the acoustic impedances in body tissues of the subject P and then received by the piezoelectric transducer elements included in the ultrasonic probe 1 as echo signals. The amplitudes of the echo signals thus received depend on the differences between the acoustic impedances on the planes of discontinuity on which the ultrasonic pulses are reflected. When the ultrasound pulses transmitted are reflected from a moving blood flow or the surface of a cardiac wall, for example, the echo signals undergo a frequency shift depending on the velocity component in the ultrasound transmission direction of the moving body because of the Doppler effect.

The monitor 2 displays a graphical user interface (GUI) through which an operator of the ultrasound diagnosis apparatus 100 inputs various instructions and setting requests using the input unit 3, and displays an ultrasonic image and analyzed results generated in the apparatus body 10.

The input unit 3 includes a mouse, a keyboard, buttons, a panel switch, a touch command screen, a foot switch, and a track ball and is connected to the apparatus body 10. The input unit 3 receives various instructions and setting requests from the operator of the ultrasound diagnosis apparatus 100 and forwards the instructions and the setting requests thus received to the apparatus body 10.

The apparatus body 10 generates an ultrasonic image on the basis of the reflected waves received by the ultrasonic probe 1. The apparatus body 10 includes, as illustrated in FIG. 1, the transmission and reception unit 11, a frame buffer 12, a B-mode processing unit 13, a Doppler processing unit 14, an image processing unit 15, an image memory 16, a control unit 17, and an internal storage unit 18.

The transmission and reception unit 11 includes, for example, a trigger generation circuit, a transmission delay circuit, and a pulsar circuit, and supplies a drive signal to the ultrasonic probe 1. The pulsar circuit repeatedly generates rate pulses for forming ultrasonic pulses at a certain pulse repetition frequency (PRF). The PRF is also called a rate frequency. The transmission delay circuit provides each of the rate pulses generated by the pulsar circuit with a transmission delay time for each piezoelectric transducer element. The transmission delay time is required to gather ultrasonic pulses generated by the ultrasonic probe 1 into a beam to determine transmission directionality. The trigger generation circuit applies a drive signal (drive pulse) to the ultrasonic probe 1 at the timing based on the rate pulse. In other words, the transmission delay circuit adjusts the transmission direction from the surface of the piezoelectric transducer elements as required by changing the transmission delay time provided to each rate pulse.

The transmission and reception unit 11 has a function that can change instantly, for example, transmission frequencies and a transmission drive voltage to implement a predetermined scan sequence, on the basis of an instruction of the control unit 17 to be described later. In particular, the transmission drive voltage is changed by a linear amplifier transmission circuit that can instantly switch values of the transmission drive voltage, or by a mechanism for switching a plurality of power units electrically.

The transmission and reception unit 11 includes an amplifier circuit, an analog/digital (A/D) converter, a reception delay circuit, an adder, and a quadrature detection circuit, and performs various types of processing on reflected wave signals received by the ultrasonic probe 1 to generate reflected wave data. The amplifier circuit amplifies the reflected wave signals for each channel to perform gain correction processing. The A/D converter A/D-converts the reflected wave signals thus gain-corrected. The reception delay circuit provides digital data with a reception delay time required to determine reception directionality. The adder performs addition processing on the reflected wave signals provided with the reception delay time by the reception delay circuit. The addition processing performed by the adder enhances reflection components along the direction in accordance with the reception directionality of the reflected wave signals. The quadrature detection circuit converts output signals from the adder into in-phase signals (I signals) and quadrature-phase signals (Q signals) in the baseband. The quadrature detection circuit stores the I signals and Q signals (hereinafter referred to as IQ signals) in the frame buffer 12 in the subsequent stage as reflected wave data. The quadrature detection circuit may convert the output signals from the adder into radio frequency (RF) signals and store them in the frame buffer 12.

The B-mode processing unit 13 receives reflected wave data from the transmission and reception unit 11 and performs processing such as logarithmic amplification and envelope demodulation to generate data (B-mode data) that represents signal intensity by using a scale of brightness.

The Doppler processing unit 14 receives the reflected wave data from the transmission and reception unit 11 to perform frequency analysis of velocity information, and extracts a blood flow, tissue and contrast agent echo components by the Doppler effect, and generates data (Doppler data) obtained by extracting moving body information such as average velocity, perfusion and power on multiple points.

The image processing unit 15 generates an ultrasonic image from the B-mode data generated by the B-mode processing unit 13 and from the Doppler data generated by the Doppler processing unit 14. Specifically, the image processing unit 15 generates a B-mode image from the B-mode data and a Doppler image from the Doppler data. The image processing unit 15 generates an ultrasonic image (B-mode image and Doppler image) as a displayed image by converting (scan-converting) a scan line signal string for ultrasonic scan into a scan line signal string in a video format typified by a TV format.

The image memory 16 stores therein an ultrasonic image generated by the image processing unit 15, and an image generated by image processing on the ultrasonic image. For example, after diagnosis, the operator can read out the images that have been stored during examination, and can use the images as still images or reproduce a plurality of images as moving images. The image memory 16 stores therein image brightness signals that have passed the transmission and reception unit 11 and other data such as raw data and image data acquired via a network, as necessary.

The control unit 17 controls overall processing performed by the ultrasound diagnosis apparatus 100. Specifically, the control unit 17 controls the transmission and reception unit 11, the B-mode processing unit 13, the Doppler processing unit 14, and the image processing unit 15, and controls the monitor 2 to display ultrasonic images stored in the image memory 16, on the basis of various instructions and setting requests input by the operator through the input unit 3 and various computer programs and setting information read from the internal storage unit 18.

The internal storage unit 18 stores therein various data such as an apparatus control program for performing ultrasound transmission and reception, image processing, and display processing; diagnostic information (patients' IDs and doctors' opinions, for example); a diagnostic protocol; and various types of setting information. The internal storage unit 18 is also used for storing images stored in the image memory 16 as necessary.

The transmission and reception unit 11 and other units installed in the apparatus body 10 may be configured by hardware such as integrated circuits, or may be configured by software programs in the form of software modules.

The following describes a case in which the ultrasound diagnosis apparatus 100 according to the first embodiment operates in the harmonic imaging mode that visualizes harmonic components. The ultrasound diagnosis apparatus 100 according to the first embodiment employs a method for cancelling fundamental components by inverting phase polarity of ultrasonic beams (hereinafter referred to as "polarity inversion").

First, the principle of the polarity inversion is described. The polarity inversion is a method for cancelling fundamental components contained in reflected wave signals to extract harmonic components by performing two rounds of ultrasound transmission and reception (transmission of ultrasonic beams and reception of reflected wave signals) along the same scan line. For example, in the first round, the ultrasound beams are transmitted in positive phase polarity, and in the second round, the ultrasound beams are transmitted in negative phase polarity, which is inverted from the phase polarity in the first round. Summation of reflected wave signals obtained from the two rounds of ultrasound transmission and reception cancels fundamental components because the phase is inverted, and enhances harmonic components that occur during transmission of ultrasound because the harmonic components are in-phase with each other.

Figure 2:
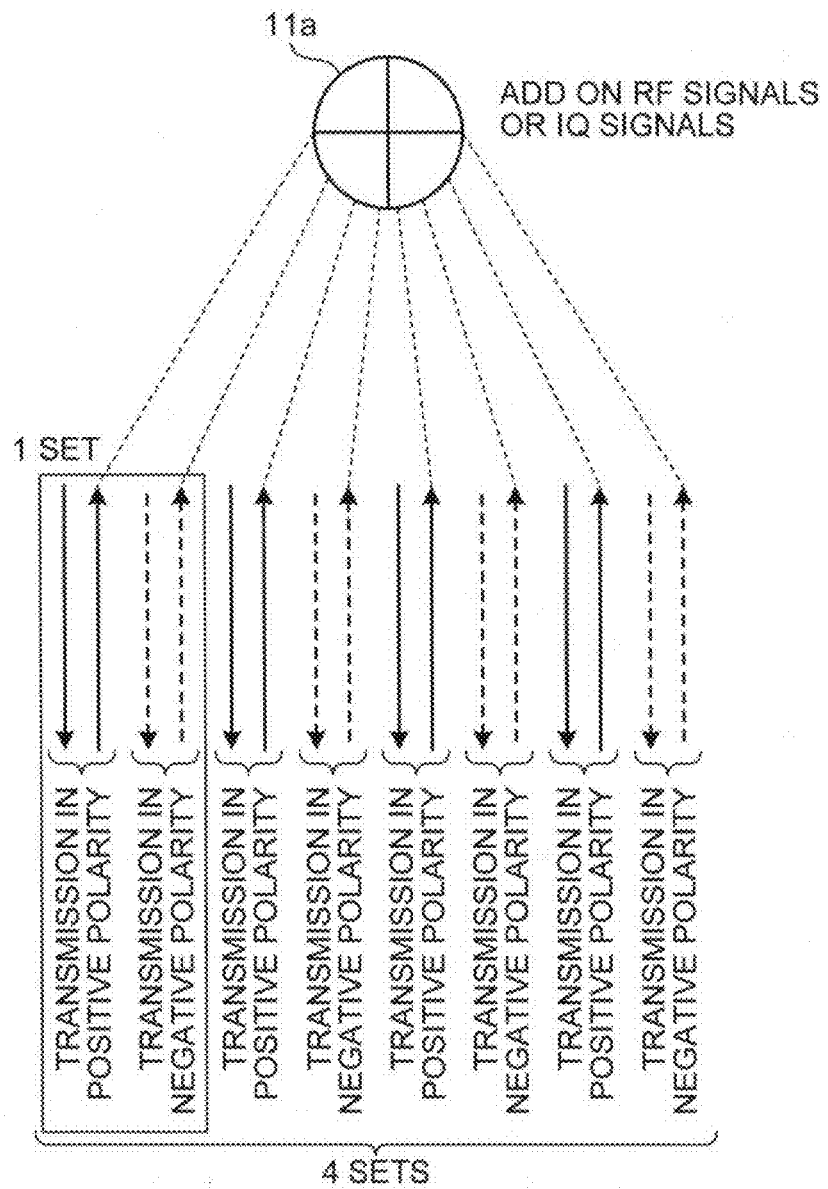
FIG. 2 is a diagram for explaining ultrasound transmission and reception according to the first embodiment.

The ultrasound diagnosis apparatus 100 according to the first embodiment performs a plurality of sets of ultrasound transmission and reception on the same scan line, each set of which is constituted of two rounds of ultrasound transmission and reception sequentially performed in reversed phase polarity along the same scan line. FIG. 2 is a diagram for explaining ultrasound transmission and reception according to the first embodiment. As illustrated in FIG. 2, a round trip of ultrasound transmission and reception performed in positive polarity (a downward solid arrow indicates transmission, and an upward solid arrow indicates reception) and a round trip of ultrasound transmission and reception performed in negative polarity (a downward dotted arrow indicates transmission and an upward dotted arrow indicates reception) constitute a set of ultrasound transmission and reception. The transmission and reception unit 11 according to the first embodiment performs, for example, four sets of ultrasound transmission and reception, each set of which is constituted of two rounds of ultrasound transmission and reception as illustrated in FIG. 2.

Performing four sets of ultrasound transmission and reception may be determined, for example, by selecting a set count (initial value) set in advance in the ultrasound diagnosis apparatus 100, or by receiving input on the set count from the operator. It may also be determined by automatically selecting a set count from a plurality of set counts set in advance in the ultrasound diagnosis apparatus 100, or by selecting a set count from a plurality of set counts using a toggle switch or other input devices by the operator.

An adder 11a included in the transmission and reception unit 11 adds reflected wave data received from a plurality of sets of ultrasound transmission and reception performed by the transmission and reception unit 11. As illustrated in FIG. 2, for example, the adder 11a adds reflected wave signals on RF signals or IQ signals. The image processing unit 15 generates an image by using the reflected wave data of a plurality of sets of ultrasound transmission and reception added by the adder 11a. In other words, reflected wave data along one scan line used by the image processing unit 15 to generate an image is obtained by adding reflected wave data of a plurality of sets of ultrasound transmission and reception.

In this case, the harmonic components as signals for generating an image increase linearly in accordance with the number of sets of transmission and reception (hereinafter referred to as "transmission and reception set count"), whereas noise components do not necessarily increase linearly because they appear at random. Consequently, the signal-to-noise ratio of the entire image including deep portions is improved, compared with a normal case in which a set of ultrasound transmission and reception constituted of two rounds of ultrasound transmission and reception is performed. When, for example, four sets of ultrasound transmission and reception, each set of which is constituted of two rounds of ultrasound transmission and reception, are performed, the signal-to-noise ratio theoretically increases by 6 dB.

Although FIG. 2 illustrates a case in which four sets of ultrasound transmission and reception are performed, the embodiment is not limited to this. The ultrasound diagnosis apparatus 100 is capable of performing n sets (n is a natural number equal to or larger than two) of ultrasound transmission and reception, each set of which is constituted of two rounds of ultrasound transmission and reception. When, for example, two sets of ultrasound transmission and reception, each set of which is constituted of two rounds of ultrasound transmission and reception, are performed, the signal-to-noise ratio theoretically increases by 3 dB. When eight sets of ultrasound transmission and reception, each set of which is constituted of two rounds of ultrasound transmission and reception, are performed, the signal-to-noise ratio theoretically increases by 9 dB.

Effects of First Embodiment

As described above, according to the first embodiment, the ultrasound diagnosis apparatus 100 performs a plurality of sets of ultrasound transmission and reception along the same scan line, each set of which is constituted of two rounds of ultrasound transmission and reception sequentially performed in reversed phase polarity along the same scan line. This enables the ultrasound diagnosis apparatus 100 to appropriately improve the sensitivity in a deep portion. In other words, according to the first embodiment, the ultrasound diagnosis apparatus 100 does not need to reduce frequencies of ultrasonic pulses, eliminating a possibility of decreased spatial resolution. The configuration according to the first embodiment is applicable to a case in which the ultrasound diagnosis apparatus 100 operates in the harmonic imaging mode, thereby effectively reducing artifacts. According to the first embodiment, the ultrasound diagnosis apparatus 100 is capable of improving the sensitivity in a deep portion while maintaining image quality.

Second Embodiment

Next described is a second embodiment. In the first embodiment, the ultrasound diagnosis apparatus 100 performs a plurality of sets of ultrasound transmission and reception, each set of which is constituted of two rounds of ultrasound transmission and reception sequentially performed in reversed phase polarity. When the ultrasound diagnosis apparatus 100 performs such ultrasound transmission and reception, the number of ultrasound transmission and reception performed along each scan line increases. Accordingly, it takes more time to collect reflected wave data for generating one frame image, thereby leading to a decrease in frame rate. The frame rate may decrease extremely in some cases depending on the number of ultrasound transmission and reception performed.

The ultrasound diagnosis apparatus 100 according to the second embodiment has a function of switching modes between one mode (hereinafter referred to as a normal mode) in which a set of ultrasound transmission and reception constituted of two rounds of ultrasound transmission and reception is performed, and the other mode (hereinafter referred to as a boost mode) in which n sets (n is a natural number equal to or larger than two) of ultrasound transmission and reception are performed, each set of which is constituted of two rounds of ultrasound transmission and reception. In other words, the ultrasound diagnosis apparatus 100 according to the second embodiment has a function of changing a balance between a frame rate and sensitivity in a deep portion.

Figure 3:
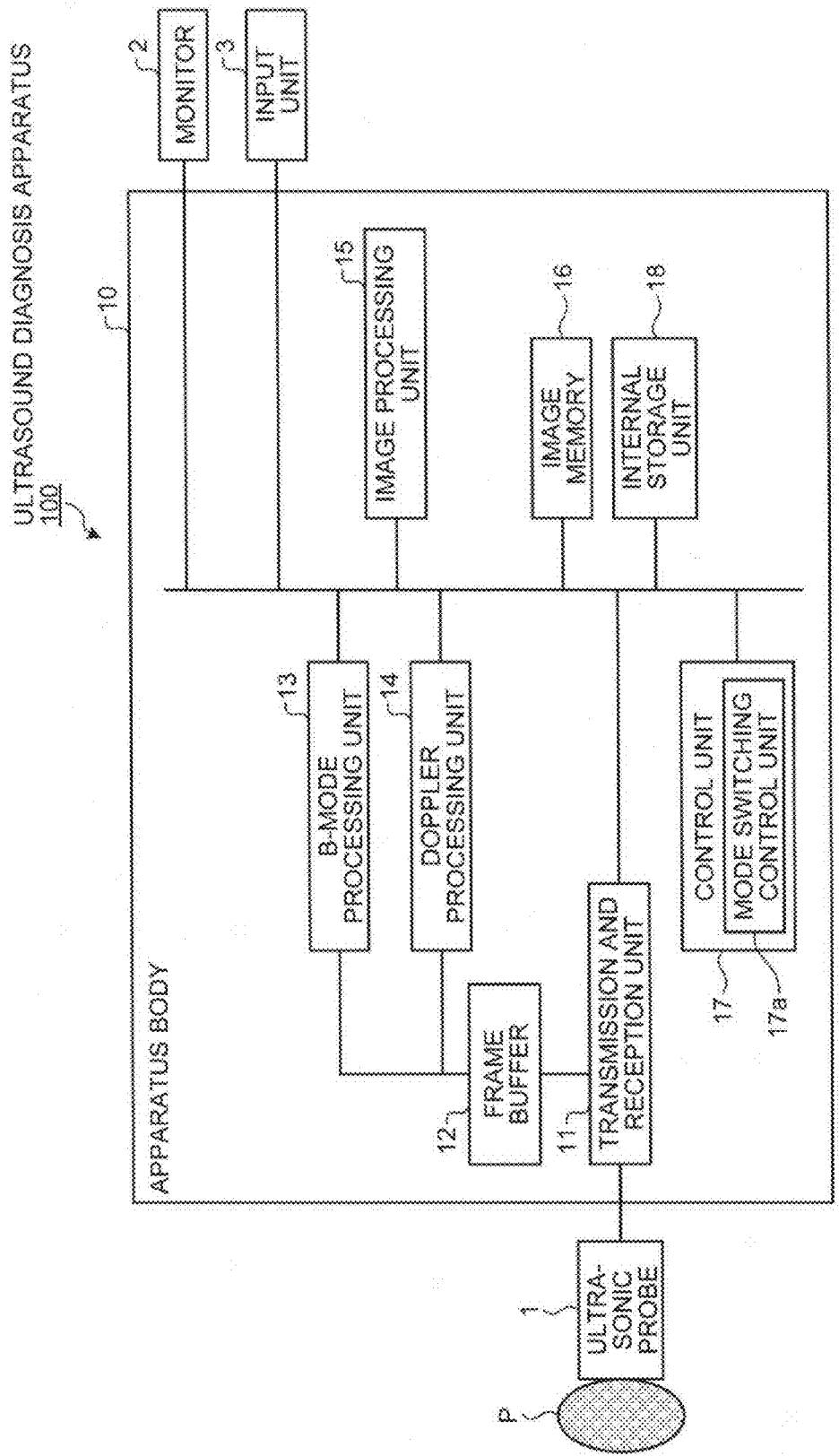
FIG. 3 is a diagram for explaining a configuration of an ultrasound diagnosis apparatus according to a second embodiment.

FIG. 3 is a diagram for explaining a configuration of the ultrasound diagnosis apparatus 100 according to the second embodiment. As illustrated in FIG. 3, although the ultrasound diagnosis apparatus 100 according to the second embodiment has the same configuration as that of the ultrasound diagnosis apparatus 100 according to the first embodiment, the ultrasound diagnosis apparatus 100 according to the second embodiment also includes a mode switching control unit 17a in the control unit 17.

Figure 4:
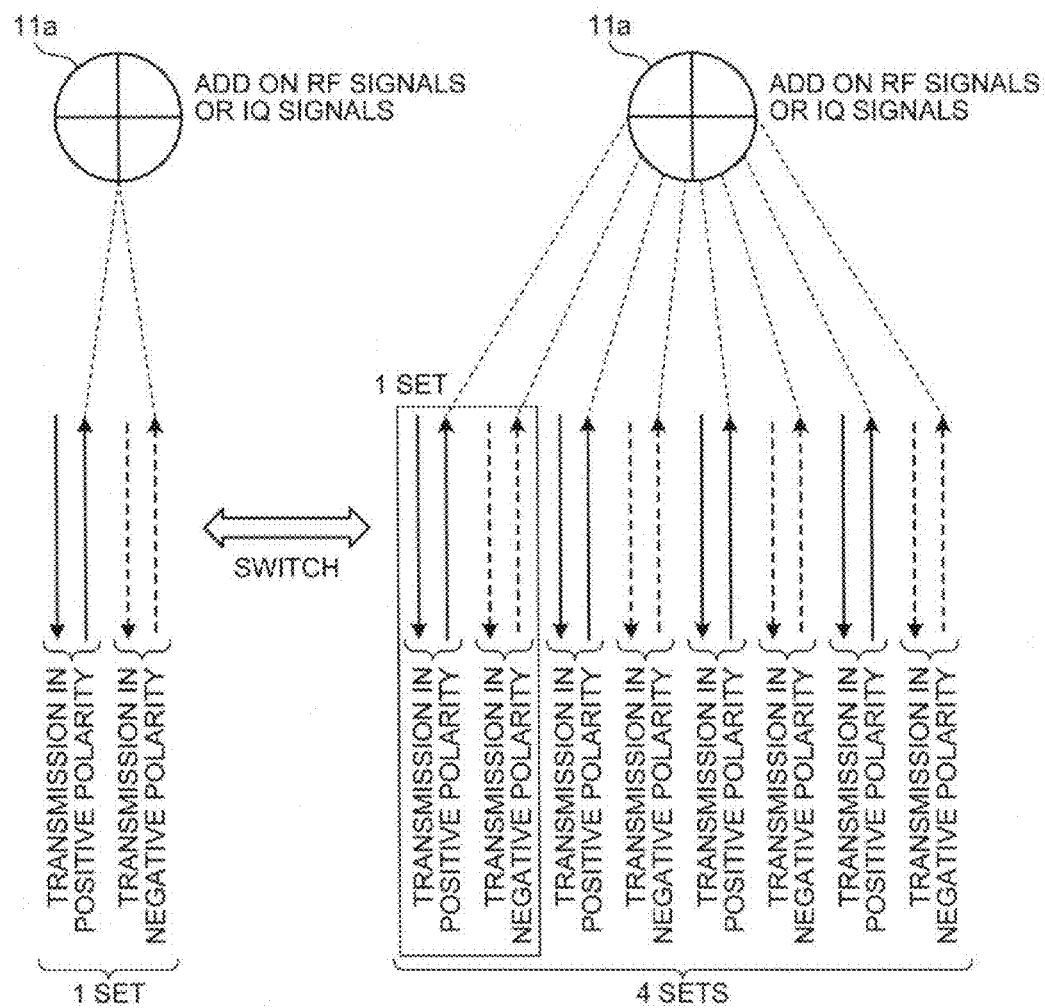
FIG. 4 is a diagram for explaining ultrasound transmission and reception according to the second embodiment.

FIG. 4 is a diagram for explaining ultrasound transmission and reception according to the second embodiment. As illustrated in FIG. 4, the mode switching control unit 17a according to the second embodiment switches the normal mode and the boost mode. The transmission and reception unit 11 according to the second embodiment performs a set or a plurality of sets of ultrasound transmission and reception depending on a switching operation by the mode switching control unit 17a.

The mode switching control unit 17a according to the second embodiment includes, for example, a selector switch on an operation table of the ultrasound diagnosis apparatus 100, serving as the input unit 3 that receives a switching instruction from the operator. When the operator operates the selector switch to "off" or "on", the mode switching control unit 17a switches the normal mode and the boost mode according to the switching operation by the operator on the selector switch. The operator of the ultrasound diagnosis apparatus 100, for example, checks an image generated in the normal mode on the monitor 2 in real time to have a rough idea of where a diagnosis region is. When finding the diagnosis region, the operator fixes the ultrasonic probe 1 on that position and switches the selector switch from "off" to "on". The mode switching control unit 17a then controls the transmission and reception unit 11 to switch the normal mode to the boost mode. The transmission and reception unit 11 stops performing a set of ultrasound transmission and reception and starts performing a plurality of sets of ultrasound transmission and reception.

Figure 5:
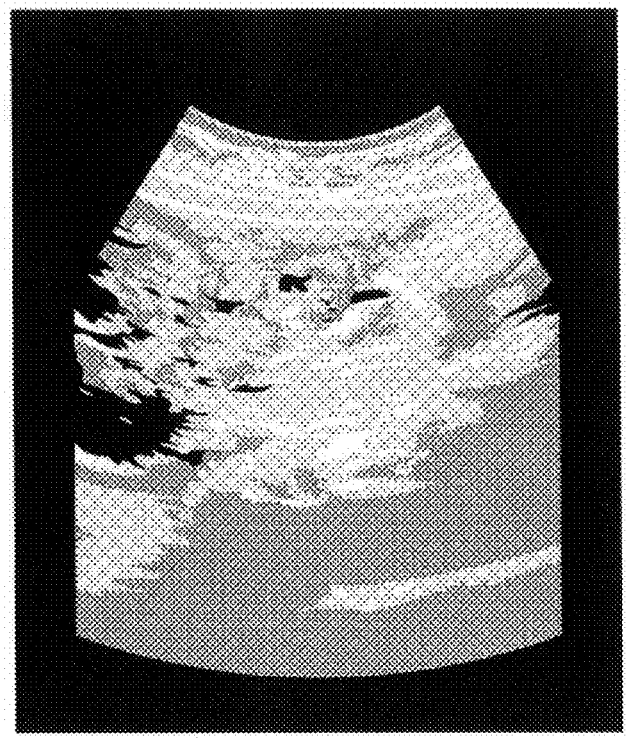
FIG. 5 is a diagram for explaining a display example according to the second embodiment.
Figure 6:
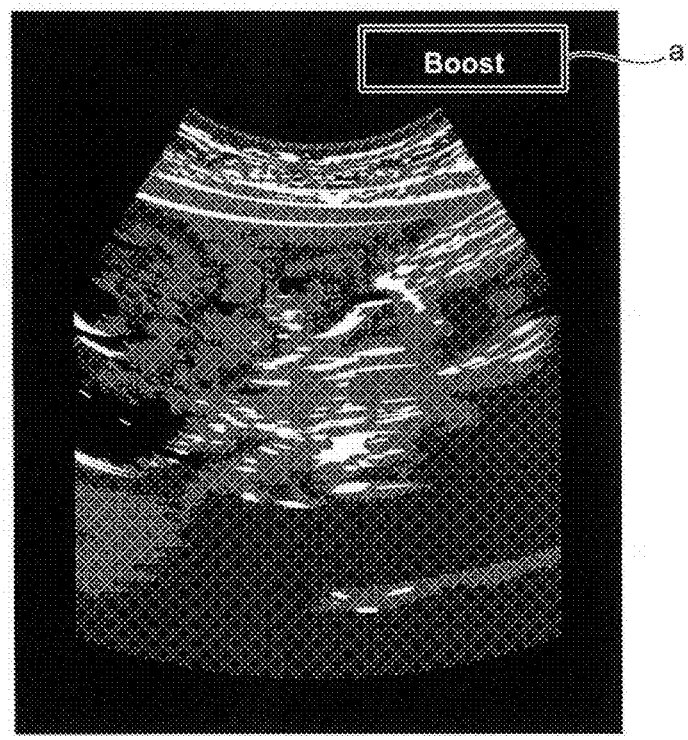
FIG. 6 is a diagram for explaining a display example according to the second embodiment.

FIGS. 5 and 6 are diagrams for explaining display examples in the second embodiment. When ultrasound transmission and reception is performed in the normal mode, the control unit 17 displays an image, for example, illustrated in FIG. 5 on the monitor 2 in real time. As illustrated in FIG. 5, sensitivity in a deep portion is low, and noises are depicted in whitish color.

When the ultrasound diagnosis apparatus 100 performs ultrasound transmission and reception in the boost mode, it collects reflected wave data at a low frame rate. In this case, the signal-to-noise ratio increases and sensitivity in the entire image including a deep portion is improved. The control unit 17 displays an image, for example, illustrated in FIG. 6 on the monitor 2 in real time. As illustrated in FIG. 6, sensitivity in a deep portion is improved, and fewer noises are depicted, compared with FIG. 5.

When the ultrasound diagnosis apparatus 100 according to the second embodiment displays an image in the boost mode, it is preferable to display, for example, "Boost" indicated by a sign a as illustrated in FIG. 6 on the monitor 2 so that the operator can recognize that the ultrasound diagnosis apparatus 100 operates in the boost mode. This enables the operator to perform diagnosis with the operator recognizing whether the image is displayed in the normal mode or in the boost mode. For example, when "Boost" is not displayed, the operator recognizes that the ultrasound diagnosis apparatus 100 operates in the normal mode, and thus the operator consciously switches the selector switch to "on". This enables the operator to perform diagnosis with an improved signal-to-noise ratio of the image.

The selector switch is not necessarily disposed on the operation table. The selector switch may be, for example, attached to the ultrasonic probe 1, or may be a pedal switch. The selector switch may be, for example, a voice switch that accepts a switching instruction from operator's voice.

The modes of the ultrasound transmission and reception are not necessarily switched by an operation on the selector switch. The modes of the ultrasound transmission and reception may be switched automatically at a timing set in advance. The mode switching control unit 17a may, for example, switch the normal mode and the boost mode once a second.

Figure 7:
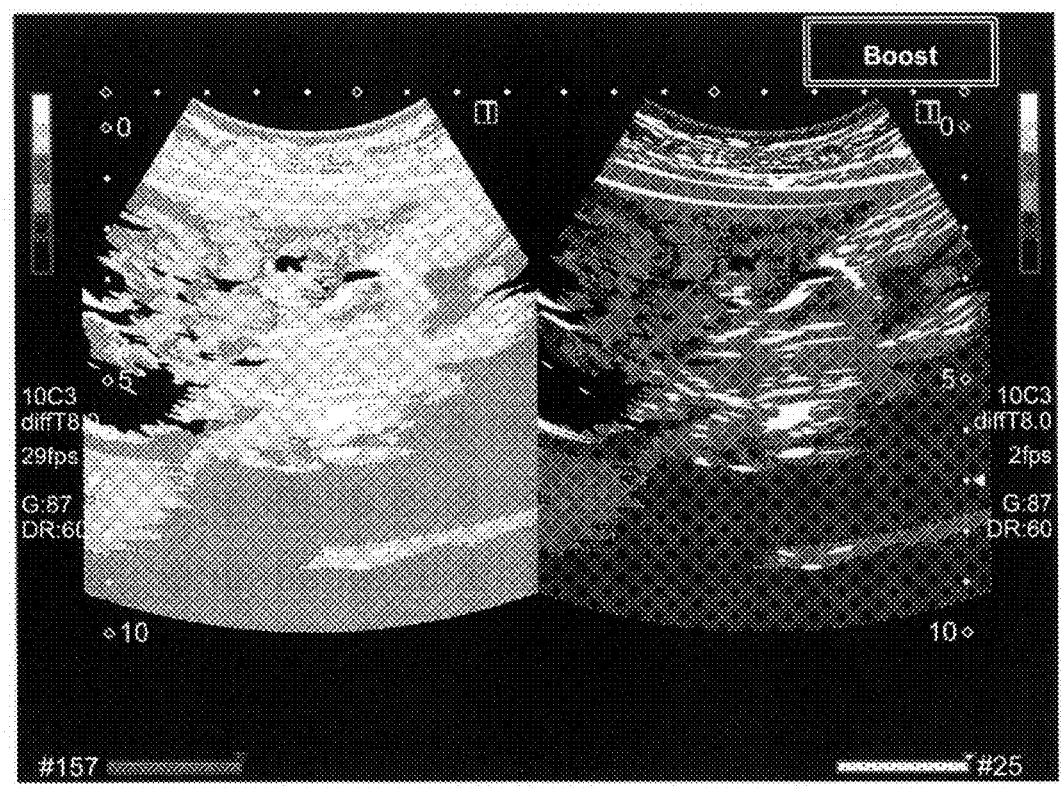
FIG. 7 is a diagram for explaining a display example according to the second embodiment.

In this case, for example, the control unit 17 may simultaneously display an image of the normal mode and an image of the boost mode side by side. FIG. 7 is a diagram for explaining a display example according to the second embodiment. As illustrated in FIG. 7, the control unit 17 displays, for example, an image of the normal mode on the left side of a display screen on the monitor 2, and an image of the boost mode on the right side thereof. The images are not necessarily displayed side by side, but may be displayed top and bottom. This enables the operator to compare the images of the normal mode and the boost mode on one screen, thereby helping the operator perform diagnosis. The control unit 17 may display one image of either mode or two images of both modes side by side in accordance with a selection operation received from the operator.

Figure 8:
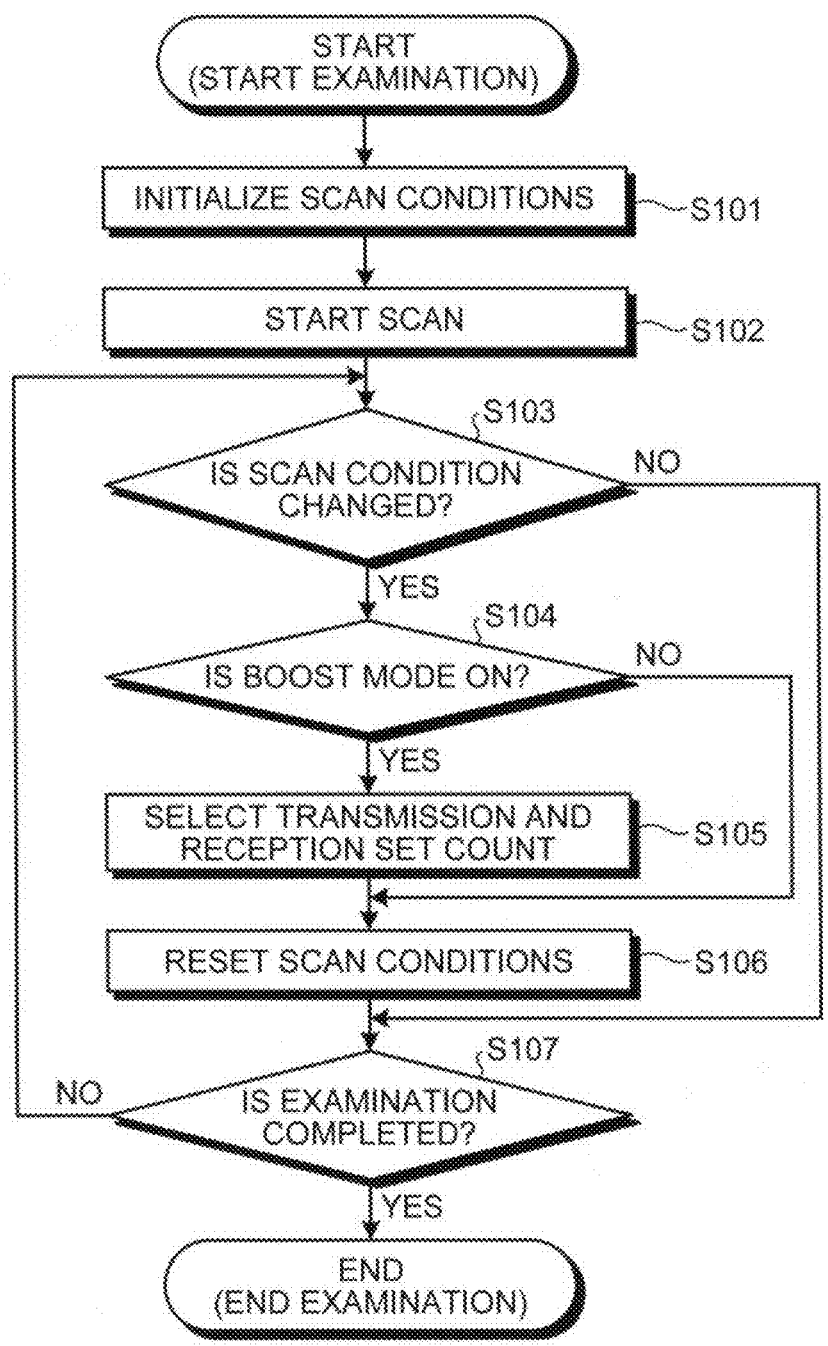
FIG. 8 is a flowchart illustrating the procedure of an examination according to the second embodiment.

Next, described is the procedure of an examination according to the second embodiment. FIG. 8 is a flowchart illustrating the procedure of the examination according to the second embodiment.

When the examination is started (start), the control unit 17 reads scan conditions set as the initial setting in the internal storage unit 18 (Step S101), and starts scanning in accordance with the initial setting thus read (Step S102). In the procedure explained in FIG. 8, the transmission and reception unit 11 first performs ultrasound transmission and reception in the normal mode.

The scan conditions are changed depending on a situation such as which part of the body will be scanned. The scan conditions include, for example, a mode of ultrasound transmission and reception, a PRF, and depth. The control unit 17 determines whether it has received an instruction to change a scan condition from the operator (Step S103). If the control unit 17 determines that it has not received such instruction (No at Step S103), the control unit 17 maintains the current scan conditions, and continues the scan started at Step S102.

If the control unit 17 determines that it has received such instruction (Yes at Step S103), the control unit 17 performs processing (Steps S104 to S106) for resetting the scan conditions.

Specifically, the control unit 17 sends an inquiry to the mode switching control unit 17a to determine whether the boost mode has already been on, or is switched to on (Step S104). If the normal mode is on (No at Step S104), the control unit 17 performs normal processing for resetting the scan conditions (Step S106).

If the boost mode is on (Yes at Step S104), the control unit 17 selects the transmission and reception set count (Step S105). For example, if the mode switching control unit 17a switches the normal mode to the boost mode at Step S104 for the first time, the control unit 17 selects the initial set count stored in the internal storage unit 18 in advance as the transmission and reception set count. If, for example, the boost mode is already on at Step S104, the control unit 17 selects another set count stored in advance as a transmission and reception set count in the internal storage unit 18, or a set count received from the operator. The transmission and reception set count may be automatically selected from a plurality of set counts stored in advance in the internal storage unit 18, or may be selected by the operator from the set counts by using, for example, the toggle switch.

The control unit 17 then calculates new scan conditions according to the changed scan condition and resets the scan conditions (Step S106). If a transmission and reception set count is selected at Step S105, the control unit 17 calculates a scan condition based on the selected transmission and reception set count to reset the scan conditions. Under the scan conditions thus reset, the control unit 17 continues scanning.

The control unit 17 then determines whether the examination is completed (Step S107). If the control unit 17 determines that the examination is not completed (No at Step S107), the process returns to Step S103, and the control unit 17 determines whether it has received an instruction to change a scan condition from the operator. If the control unit 17 determines that the examination is completed (Yes at Step S107), the control unit 17 ends the scan and the examination.

Effects of Second Embodiment

As described above, the ultrasound diagnosis apparatus 100 according to the second embodiment performs ultrasound transmission and reception by switching modes between the normal mode in which a set of ultrasound transmission and reception is performed, and the boost mode in which a plurality of sets of ultrasound transmission and reception are performed. This enables the operator to switch to the boost mode as necessary, thereby preventing a decrease in frame rate.

Additional Functions of Second Embodiment

Described above is the ultrasound diagnosis apparatus 100 according to the second embodiment that has a function of switching the normal mode and the boost mode. The switching function described above is performed based on an operation by the operator or automatically performed at a timing set in advance. As described above, the ultrasound diagnosis apparatus 100 according to the second embodiment displays an image in each mode separately, or images in both modes simultaneously, as a displaying function. The ultrasound diagnosis apparatus 100 can optionally select and combine the functions described above. In addition, the ultrasound diagnosis apparatus 100 can also optionally select and combine additional functions described below.

Additional Function 1: Automatic Switching Based on Detection of Image Change, Etc.

Although the second embodiment describes a method for automatically switching the normal mode and the boost mode at a timing set in advance, the embodiment is not limited to this. When the operator tries to increase sensitivity of an image, the operator fixes the ultrasonic probe 1 on the current position and instructs the subject P to stop breathing in many cases. The mode switching control unit 17a according to the second embodiment may detect, for example, changes such as "change in the image becomes smaller" or "motion of the ultrasonic probe 1 becomes smaller" to use such detection results as a trigger to automatically switch to the boost mode. Specifically, the mode switching control unit 17a detects a change in a subject region to be analyzed by using the reflected wave data, or motion of the ultrasonic probe 1 by adding a magnetic sensor thereto, and switches the normal mode to the boost mode on the basis of the detected change in the subject region or the detected motion.

The mode switching control unit 17a, for example, acquires frames generated by the image processing unit 15 as needed, and calculates a correlational value between the frames as needed. When detecting that the calculated correlational value exceeds a threshold set in advance, the mode switching control unit 17a switches the normal mode to the boost mode. Thereafter, when the operator moves the ultrasonic probe 1, the correlational value between the frames becomes smaller than the threshold set in advance. In this case, when the mode switching control unit 17a detects that the calculated correlational value falls below the threshold set in advance, the mode switching control unit 17a switches the boost mode to the normal mode.

Figure 9:
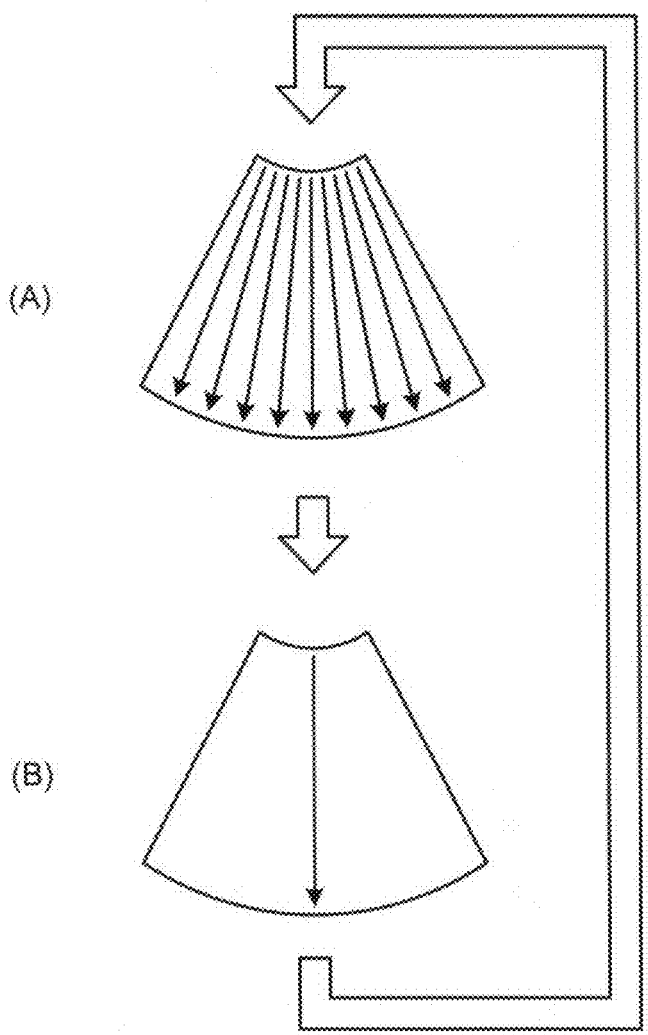
FIG. 9 is a diagram for explaining ultrasound transmission and reception dedicated to motion detection according to the second embodiment.

FIG. 9 is a diagram for explaining ultrasound transmission and reception dedicated to motion detection according to the second embodiment. As illustrated in FIG. 9(A), for example, the mode switching control unit 17a performs normal ultrasound transmission and reception for generating an image, and as illustrated in FIG. 9(B), the mode switching control unit 17a performs ultrasound transmission and reception dedicated to motion detection at a certain timing, thereby repeating the normal ultrasound transmission and reception and the ultrasound transmission and reception dedicated to motion detection. The mode switching control unit 17a then calculates, as needed, a correlational value between beams (reflected wave data) on the same scan line obtained by the ultrasound transmission and reception dedicated to motion detection. When detecting that the calculated correlational value exceeds a threshold set in advance, the mode switching control unit 17a switches the normal mode to the boost mode. Thereafter, when the operator moves the ultrasonic probe 1, the correlational value between the beams falls below the threshold set in advance. In this case, the mode switching control unit 17a detects that the calculated correlational value falls below the threshold set in advance, and switches the boost mode to the normal mode.

The embodiment is not limited to the method for performing ultrasound transmission and reception dedicated to motion detection. The embodiment may employ, for example, a method for calculating a correlational value between beams along a scan line in the normal ultrasound transmission and reception for generating an image.

When, for example, the mode switching control unit 17a receives, from the ultrasonic probe 1, information obtained by a sensor attached to the ultrasonic probe 1, and determines that the ultrasonic probe 1 is stopped from the information, the mode switching control unit 17a switches the normal mode to the boost mode. Thereafter, when the operator moves the ultrasonic probe 1, the mode switching control unit 17a determines that the ultrasonic probe 1 starts moving from the information obtained by the sensor, and switches the boost mode to the normal mode.

Additional Function 2: Boost Mode for a Part of a Region

Although the second embodiment describes a method for applying the boost mode to the entire region of an image, the embodiment is not limited to this. The boost mode may be applied only to a part of a region of an image, while the normal mode may be applied to the other part of the region. In this case, a decrease in frame rate can be prevented.

Figure 10:
FIG. 10 is a diagram for explaining a boost mode according to the second embodiment.

FIG. 10 is a diagram for explaining the boost mode according to the second embodiment. The mode switching control unit 17a, for example, controls the transmission and reception unit 11 to switch to the boost mode only in a region indicated by a sign b. The region indicated by the sign b may be automatically set in the center part of the image, or may be specified by the operator. In FIG. 10, although the region indicated by the sign b has a rectangle shape, for example, the embodiment is not limited to this. The region may be set in any shape or in any position. As illustrated in FIG. 10, it is preferable to display, for example, "Boost" indicated by a sign c on the monitor 2 so that the operator can recognize that the ultrasound diagnosis apparatus 100 operates in the boost mode.

Additional Function 3: Storing of Image in Conjunction with Switching of Modes

According to the second embodiment, the ultrasound diagnosis apparatus 100 may freeze or store an image in conjunction with switching of modes. For example, the control unit 17 may pause (freeze) an image generated by the image processing unit 15 and output to the monitor 2, which is triggered by switching to the boost mode by the mode switching control unit 17a. The control unit 17 includes, for example, a storage control unit (not illustrated). The storage control unit may store, in the image memory 16, an image generated by the image processing unit 15, which is triggered by switching to the boost mode by the mode switching control unit 17a. When collecting an image with a high signal-to-noise ratio, the operator freezes the image for observation, and stores the image in many cases. Switching of modes in conjunction with freezing and storing of an image enables the operator to efficiently acquire and store a high quality image, thereby improving efficiency in examinations.

Third Embodiment

Next described is a third embodiment. In the first embodiment or the second embodiment, the number of sets of ultrasound transmission and reception, each set of which is constituted of two rounds of ultrasound transmission and reception sequentially performed in reversed phase polarity is determined, for example, by using a transmission and reception set count set in advance, or by receiving an input of a transmission and reception set count from the operator. The ultrasound diagnosis apparatus 100 according to the third embodiment calculates correlation between frames or between beams on the same scan line to detect motion of a biological body or the ultrasonic probe 1, thereby automatically determining the optimal transmission and reception set count in accordance with a situation.

In the boost mode, increasing the transmission and reception set count is advantageous from a sensitivity point of view because sensitivity increases as the transmission and reception set count increases. In general, an increased transmission and reception set count results in a longer time to collect reflected wave data. Consequently, when a subject region moves, a phase shift may occur due to the move. The phase shift appears as a position shift in an image. When creating an image, the ultrasound diagnosis apparatus 100 adds several pieces of reflected wave data that contain the position shift occurring as a result of a move in the subject region. This may cause deterioration of resolution or decrease in contrast, thereby failing to improve sensitivity as expected. When the operator examines a subject region that moves a lot, such as the heart or a beating artery, the motion of the subject region significantly affects an image to be generated. Thus, the transmission and reception set count needs to be reduced. In other words, the transmission and reception set count needs to be adjusted depending on which region to examine: when the operator examines a subject region that moves little, the transmission and reception set count is increased, whereas, when the operator examines a subject region that moves a lot, the transmission and reception set count is reduced.

The second embodiment employs a method that allows the operator to select a transmission and reception set count, for example. This requires the operator to change the transmission and reception set count manually every time the subject region is changed. Moreover, it is difficult for the operator to intuitively make the optimal decision as to how many sets of transmission and reception are performed, or make appropriate determination as to how much the movement of a subject region affects an image. Thus, the operator needs to repeat trial and error until the operator finds the optimal value, which may cause deterioration in examination throughputs. In order to limit the deterioration in examination throughputs to a minimum, the ultrasound diagnosis apparatus 100 can only have limited options for the transmission and reception set count. Thus, it is difficult for the ultrasound diagnosis apparatus 100 to provide the optimal transmission and reception set count for every subject to be examined that moves differently depending on a situation (a person or a region).

Figure 11:
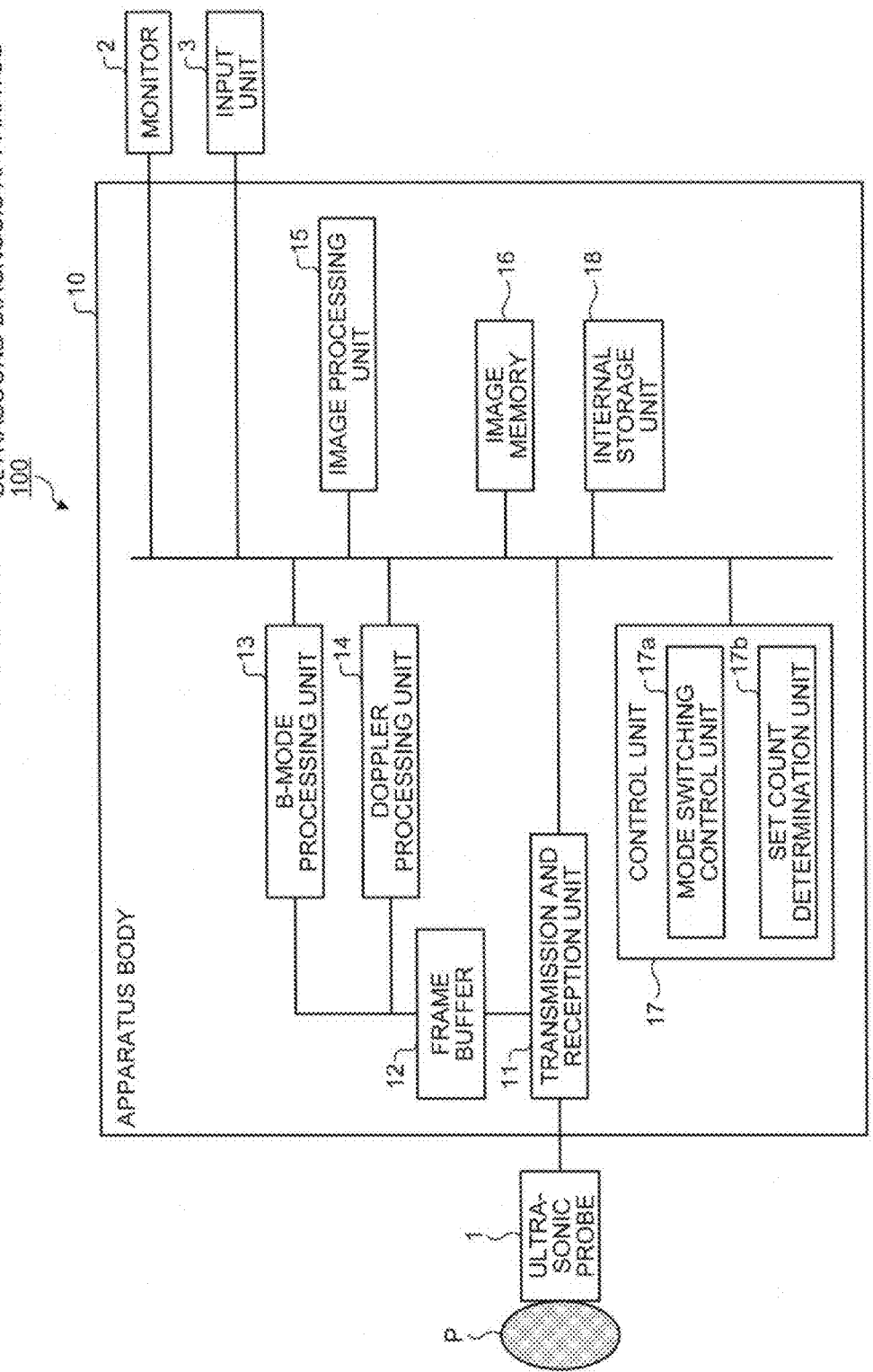
FIG. 11 is a diagram for explaining a configuration of an ultrasound diagnosis apparatus according to a third embodiment.

FIG. 11 is a diagram for explaining a configuration of the ultrasound diagnosis apparatus 100 according to the third embodiment. As illustrated in FIG. 11, although the ultrasound diagnosis apparatus 100 according to the third embodiment has the same configuration as that of the ultrasound diagnosis apparatus 100 according to the first embodiment, it also includes the mode switching control unit 17a and a set count determination unit 17b in the control unit 17. The set count determination unit 17b detects motion occurring in a subject region. The set count determination unit 17b determines a transmission and reception set count on the basis of the motion thus detected. The transmission and reception unit 11 according to the third embodiment performs ultrasound transmission and reception in accordance with the set count determined by the set count determination unit 17b.

Figure 12:
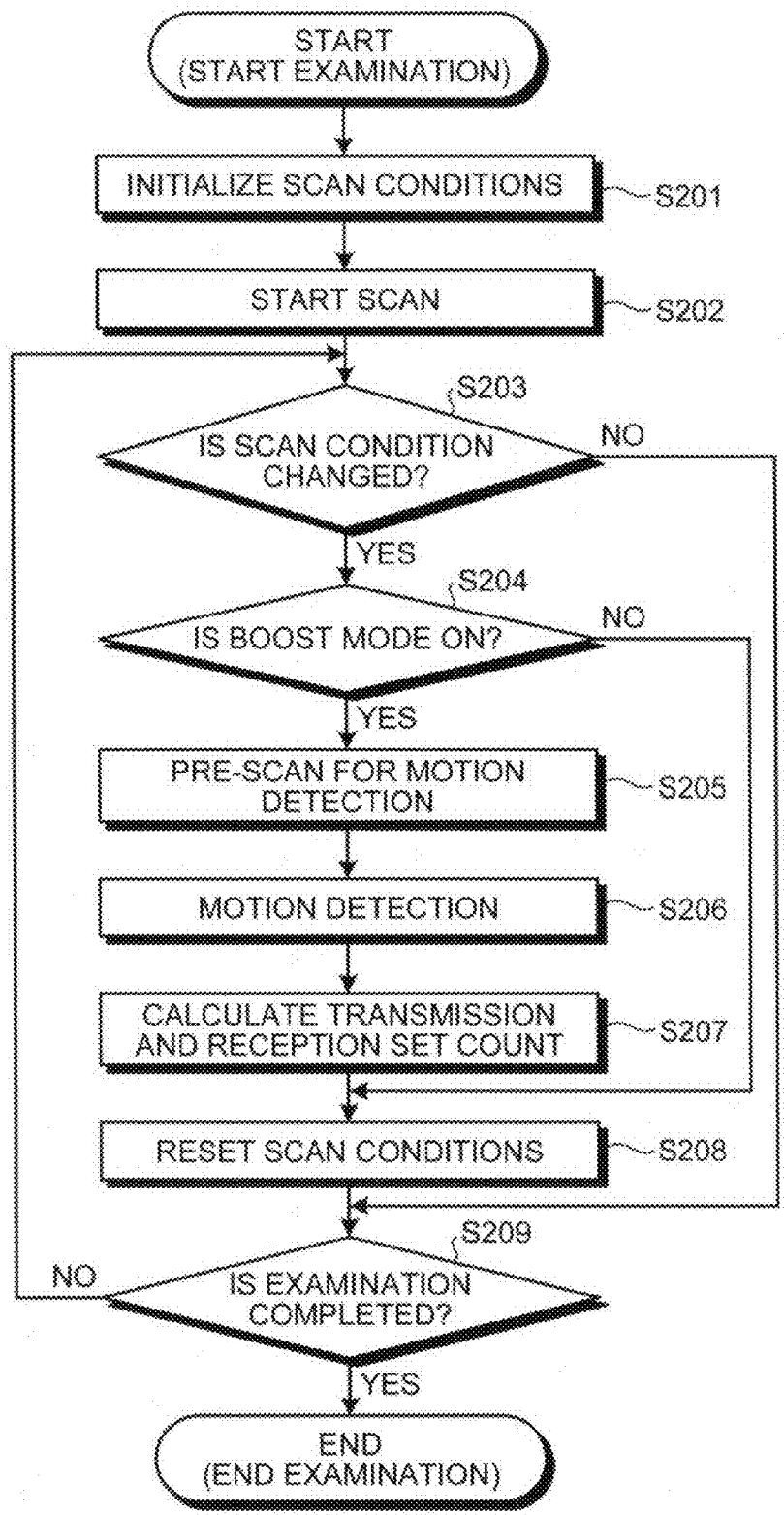
FIG. 12 is a flowchart illustrating the procedure of an examination according to the third embodiment.

First, described is the procedure of an examination according to the third embodiment. FIG. 12 is a flowchart illustrating the procedure of the examination according to the third embodiment.

Processing from Steps S201 to S203 is performed in the same manner as in the second embodiment. That is, when the examination is started, the control unit 17 reads the initial setting of scan conditions from the internal storage unit 18 (Step S201), and starts scanning in accordance with the initial setting thus read (Step S202). The control unit 17 determines whether it has received an instruction to change a scan condition from the operator (Step S203). If the control unit 17 determines that it has not received such instruction (No at Step S203), the control unit 17 maintains the current scan conditions, and continues the scan started at Step S202. If the control unit 17 determines that it has received such instruction (Yes at Step S203), the control unit 17 performs processing (Steps S204 to S207) for resetting the scan conditions.

Specifically, the control unit 17 sends an inquiry to the mode switching control unit 17a to determine whether the boost mode has already been on, or is switched to on (Step S204). If the normal mode is on (No at Step S204), the control unit 17 performs normal processing for resetting the scan conditions (Step S208).

If the boost mode is on (Yes at Step S204), the control unit 17 according to the third embodiment performs pre-scan for detecting motion in the subject region (Step S205). The pre-scan is performed for the purpose of determining a transmission and reception set count, and is not necessarily performed under the same scan conditions as those for generating an image. For example, scan conditions such as the number of beams and the number of focus positions may be changed. The pre-scan may collect reflected wave data on a frame basis as performed in the B-mode scan, or may collect the reflected wave data on a scan line (raster) basis, or on an alternate scan line basis as performed in color Doppler imaging (CDI). It is preferable to perform pre-scan suitable for the processing for analyzing motion to be described later.

The set count determination unit 17b detects motion in the subject region by using the reflected wave data collected in the pre-scan (Step S206). The set count determination unit 17b calculates a transmission and reception set count on the basis of the motion detected (Step S207). There are two methods for determining a transmission and reception set count: one is a method using frame-to-frame correlation (hereinafter referred to as a frame correlation method); and the other is a method using beam-to-beam correlation on the same scan line (hereinafter referred to as a beam correlation method). These methods will be described later in detail.

Thereafter, as in the case of the second embodiment, the control unit 17 calculates new scan conditions according to the changed scan condition and resets the scan conditions (Step S208). If the examination is not completed (No at Step S209), the process returns to the processing at which the control unit 17 determines whether it has received an instruction to change a scan condition from the operator. If the examinations is completed (Yes at Step S209), the control unit 17 ends the scan and the examination.

In the second and the third embodiments described above, although the control unit 17 determines whether the boost mode has already been on, or the boost mode is switched to on to perform the processing for determining a transmission and reception set count, the embodiment is not limited to this. For example, the control unit 17 may perform the processing for determining a transmission and reception set count, triggered by a change in depth condition that changes, for example, the PRF, or a change in the subject region that changes a frame rate.

Although a method for performing pre-scan for motion detection is described, the embodiment is not limited to this. When, for example, the control unit 17 already started scanning for generating an image, the control unit 17 may detect motion by analyzing the frames and beams collected in the scan.

As described above, two methods are mainly assumed in the third embodiment for the set count determination unit 17b to determine a transmission and reception set count. One is the frame correlation method, and the other is the beam correlation method. The following describes the methods in the order.

First, described is the frame correlation method. In the third embodiment, for example, it is assumed that the control unit 17 collects, as the pre-scan, reflected wave data frame by frame as in the case of the B-mode scan for a certain time period.

When reflected wave data of n frames is collected, the set count determination unit 17b calculates correlational values of frames relative to, for example, the first frame. For example, the set count determination unit 17b calculates correlational values between the first frame and the second frame, the first frame and the third frame, up to the first frame and the nth frame. It is expected that correlation between frames decreases as a time-phase difference between the frames increases from which correlational values are calculated. This enables the set count determination unit 17b to specify collection time within which the influence of motion can be suppressed, by determining in what frame the correlational value falls below a threshold set in advance.

When, for example, scan conditions for the pre-scan and scan conditions for the normal scan are the same, and the correlational value between the first frame and the eleventh frame falls below the threshold, collection time for up to ten frames is a tolerable range with respect to motion. When reflected wave data for one frame is collected in a collection time of ten frames, the set count determination unit 17b determines that the transmission and reception set count "10" is the optimal transmission and reception set count as long as only the transmission and reception set count is changed among the scan conditions.

In the frame correlation method, the set count determination unit 17b may calculate correlational values between frames as described above, and may also calculate correlational values between local regions of respective frames. When the set count determination unit 17b calculates correlational values between local regions, the number of regions per frame may be one or larger than one.

The frame correlation method is not limited to the method described above. The set count determination unit 17b may first calculate a correlational value between two frames, and then calculate a transmission and reception set count by using a relational expression set in advance, substituting the calculated correlational value.

For example, the relation between a velocity of motion and a suitable collection time is obtained in advance from, for example, an experiment, and a relational expression is set. The velocity of motion can be calculated from a correlational value between frames and a frame rate. For example, a velocity of motion is calculated from a correlational value between frames and a frame rate, and the velocity of movement thus calculated is substituted in the relational expression, whereby a suitable collection time can be obtained. Furthermore, setting in advance a relational expression between a collection time and a PRF enables the set count determination unit 17b to calculate a suitable transmission and reception set count by substituting the collection time thus obtained in the relational expression.

The set count determination unit 17b may use, for example, a table that contains correlational values between frames and transmission and reception set counts that are associated with each other in advance. This table is generated by, for example, an experiment conducted in advance. It is desirable that the table can be changed, and that a plurality of tables are provided for respective frame rates of the pre-scan, for example.

The set count determination unit 17b may calculate correlational values between the first frame and the second frame, the second frame and the third frame, and up to the (n−1)th frame and the nth frame to obtain the maximum value and the minimum value in the correlational values. The set count determination unit 17b may then determine a transmission and reception set count by using a relational expression or a table corresponding to the maximum and minimum values.

Next, the beam correlation method is described. The set count determination unit 17b calculates motion velocity of biological signals by using the same principle as the CDI principle, in particular, the tissue Doppler imaging (TDI) principle that uses, what is called, the Doppler effect. In this case, two-dimensional velocity mapping is possible. The set count determination unit 17b calculates a transmission and reception set count by using the maximum velocity and the average velocity of the motion velocity in a subject region. The set count determination unit 17b may calculate a transmission and reception set count by using a relational expression or a table as used in the case of the frame correlation method. The set count determination unit 17b may use, for example, a relational expression between a motion velocity and a transmission and reception set count obtained from an experiment conducted in advance. The set count determination unit 17b may use, for example, a table that contains moving velocities and transmission and reception set counts that are associated with each other in advance. The set count determination unit 17b may perform threshold processing as performed in the case of the frame correlation method.

The ultrasound diagnosis apparatus 100 according to the third embodiment may display a certain indicator that represents how much the detected biological body and the ultrasonic probe 1 are moved, and may also display values such as calculated correlational values and a motion velocity. The control unit 17 may, for example, store in advance a relational expression for indicating the correlation between "motion of a biological body or the ultrasonic probe 1" and "holding accuracy of the ultrasonic probe 1". When the set count determination unit 17b detects motion, it may substitute a detected value into the relational expression and calculate an indicator indicating the holding accuracy of the ultrasonic probe 1, and may display the indicator thus calculated on the monitor 2. When the motion is smaller, for example, the indicator indicating the holding accuracy has a higher value. The control unit 17 may, for example, store a relational expression for indicating the correlation between "motion of a biological body or the ultrasonic probe 1" and "an indicator indicating influence of cardiac beat" in advance. When the set count determination unit 17b detects motion, it may substitute a detected value in the relational expression and calculate an indicator indicating the influence of cardiac beat, and may display the indicator thus calculated on the monitor 2. When the motion is smaller, for example, the indicator indicating the influence of cardiac beat has a lower value. The control unit 17 may, for example, display values such as calculated correlational values and a moving velocity in a form of color coding in which different colors are assigned depending on the values. When the control unit 17 displays how much a biological body or the ultrasonic probe 1 is moved in a form of a certain indicator, the control unit 17 may also display a color-coded indicator.

The ultrasound diagnosis apparatus 100 according to the third embodiment may freeze or store an image in conjunction with motion of a detected biological body or the ultrasound probe 1. When, for example, the ultrasound diagnosis apparatus 100 performs scanning for generating an image and detects motion by analyzing frames or beams collected in the scan, the control unit 17 may freeze an image generated by the image processing unit 15 and output to the monitor 2, triggered by determining that the motion detected by the set count determination unit 17b falls below a threshold set in advance. The storage control unit included in the control unit 17 may, for example, store an image generated by the image processing unit 15 in the image memory 16, triggered by determining that the motion detected by the set count determination unit 17b falls below a threshold set in advance.

Effects of Third Embodiment

According to the third embodiment described above, the ultrasound diagnosis apparatus 100 can automatically determine the transmission and reception set count, thereby improving the examination throughput. The ultrasound diagnosis apparatus 100 can determine an optimal transmission and reception set count according to a state of motion, thereby contributing to improvement in diagnosis.

Additional Function 1: Change in Threshold, Etc., for Determining Transmission and Reception Set Count As described above, the set count determination unit 17b determines a transmission and reception set count by using, for example, a threshold, a relational expression, and a table that are set in advance. The ultrasound diagnosis apparatus 100 may include a user interface (UI) for receiving changes in, for example, the threshold, the relational expression, and the table. The ultrasound diagnosis apparatus 100 may control the set count determination unit 17b to perform determination processing (Steps S205 to S207 in FIG. 12), triggered by receiving a change in the threshold, the relational expression, or the table.

Additional Function 2: Change in Transmission and Reception Set Count in Real Time In the third embodiment, a method is described in which the set count determination unit 17b detects motion in a subject region by analyzing reflected wave data collected through the pre-scan, but the embodiment is not limited to this. For example, a magnetic sensor is attached to the ultrasonic probe 1 to detect motion of the ultrasonic probe 1.

The control unit 17 according to the third embodiment may, for example, automatically change a gain value used to amplify the reflected wave signals received at the amplifier circuit, in accordance with the normal mode or the boost mode, or in accordance with the transmission and reception set count. Normally, a gain value needs to be changed in conjunction with switching of modes, or a change in the transmission and reception set count. Thus, the control unit 17 may, for example, automatically change the gain value in conjunction with switching of the normal mode and the boost mode, or a change in the transmission and reception set count. This is efficient and convenient for the operator. Compared with the normal mode, both signals (S) and noises (N) increase in the boost mode. It is preferable, in general, to reduce gain in the boost mode. When a large number of transmission and reception set count is set, it is also preferable to reduce gain. When, for example, the mode switching control unit 17a switches the normal mode to the boost mode, the control unit 17 reduces the gain value set in the amplifier circuit. When, for example, the set count determination unit 17b determines to increase the transmission and reception set count, the control unit 17 also reduces the gain value set in the amplifier circuit.

When, for example, the ultrasound diagnosis apparatus 100 is performing scanning in the boost mode, the set count determination unit 17b may detect motion by continuously or intermittently monitoring the collected frames and beams. When velocity of motion is changed during the scanning in the boost mode, the set count determination unit 17b can calculate and determine the transmission and reception set count corresponding to the changed velocity. This enables the ultrasound diagnosis apparatus 100 to detect influence of motion adaptively without waiting for an instruction from the operator, and to examine a subject region under optimal conditions at any time. In this case, the ultrasound diagnosis apparatus 100 may perform ultrasound transmission and reception dedicated to motion detection as explained by using FIG. 9 according to the second embodiment.

Other Embodiments

Although the ultrasound diagnosis apparatus 100 according to the first to the third embodiments is described, the embodiments are not limited to this. For example, the ultrasound diagnosis apparatus 100 according to any one of the first to the third embodiments can use the functions described in the first embodiment, the functions described in the second embodiment, and the functions described in the third embodiment. Although a plurality of functions are listed and described, the ultrasound diagnosis apparatus 100 according to any one of the first to the third embodiments can include a part or all of the functions.

Three or More Types of Modes

Although in the second and the third embodiments, a method is described in which the ultrasound diagnosis apparatus 100 switches two types of modes (the normal mode and the boost mode), the embodiments are not limited to this. The ultrasound diagnosis apparatus 100 may switch three or more types of modes. For example, the ultrasound diagnosis apparatus 100 may switch modes among the normal mode and two or more types of modes that have a different transmission and reception set count.

Other Imaging Modes Such as B-Mode

Although the first to the third embodiments describe a case in which the ultrasound diagnosis apparatus operates in the harmonic imaging mode, the embodiments are not limited to this. Even when the ultrasound diagnosis apparatus operates in the normal B-mode or in the CDI (in particular, the TDI) mode, the configurations described in the first to the third embodiments are also applicable. In this case, the ultrasound diagnosis apparatus includes the transmission and reception unit, the addition unit, and the image generation unit. The transmission and reception unit performs ultrasound transmission and reception for receiving reflected wave data necessary to generate an image a plurality of times on the same scan line. The addition unit adds reflected wave data received from a plurality of times of ultrasound transmission and reception performed by the transmission and reception unit. The image generation unit generates an image by using the reflected wave data of a plurality of times of ultrasound transmission and reception added by the addition unit. For example, the transmission and reception unit performs ultrasound transmission and reception four times along the same scan line under the same scan conditions. The addition unit adds reflected wave data received from the four times of ultrasound transmission and reception performed on the same scan line. The image generation unit generates an image by using the reflected wave data of the four times of ultrasound transmission and reception added by the addition unit. The embodiments are not limited to a case in which the ultrasound diagnosis apparatus operates in the harmonic imaging in the polarity determination method. The embodiments are also applicable to a case in which the ultrasound diagnosis apparatus operates in the harmonic imaging in the filtering method.

The third embodiment describes a method for determining a transmission and reception set count by using the frame correlation method or the beam correlation method. The ultrasound diagnosis apparatus may select a method depending on in what mode the ultrasound diagnosis apparatus performs scanning. When, for example, the ultrasound diagnosis apparatus performs scanning in the B-mode, it selects the frame correlation method, whereas, when the ultrasound diagnosis apparatus performs scanning in the CDI (in particular the TDI) mode, it selects the beam correlation method.

Others

The embodiments are not limited to a case in which the ultrasound diagnosis apparatus generates a two-dimensional image. The embodiments are also applicable to a case in which the ultrasound diagnosis apparatus generates a three-dimensional image. The embodiments are also applicable to a case in which the ultrasound diagnosis apparatus performs contrast imaging. In this case, the ultrasound diagnosis apparatus can increase sensitivity in a deep portion without increasing acoustic pressure. When performing contrast imaging, the ultrasound diagnosis apparatus can further improve contrast by switching modes and adjusting acoustic pressure simultaneously. For example, when performing ultrasound transmission and reception in the boost mode, the ultrasound diagnosis apparatus reduces acoustic pressure to suppress, for example, destruction of bubbles. This leads to further improvement in contrast.

The ultrasound diagnosis apparatus according to at least one of the embodiments described above can increase sensitivity in a deep portion appropriately.

While certain embodiments have been described, these embodiments have been presented by way of example only, and are not intended to limit the scope of the disclosure. Indeed, the novel apparatus described herein may be embodied in a variety of other forms; furthermore, various omissions, substitutions and changes in the form of the apparatus described herein may be made without departing from the spirit of the disclosure. The accompanying claims and their equivalents are intended to cover such forms or modifications as would fall within the scope and spirits of the disclosure.

What is claimed is:
1. An ultrasound diagnosis apparatus, comprising:
processing circuitry configured to
select one of a plurality of imaging modes including a first mode to prevent as decrease in frame rate and a second mode to increase sensitivity in a deep portion, according to an operation from an operator,
cause an ultrasound probe to execute a set of ultrasound transmissions/receptions a first set number of times for each of a plurality of scanning lines when the first mode is selected and execute the set of the ultrasound transmissions/receptions continuously a second set number of times for each of the plurality of scanning lines so as to maintain a spatial resolution of the first mode when the second mode is selected, the set of ultrasound transmissions/receptions being constituted of two rounds of an ultrasound transmission/reception along a same scanning line with reversed phase polarity, the second set number being plural and larger than the first set number, the first set number and the second set number being positive integers;

obtain a first set of reflected waves, for each scanning line, as a result of the executing the set of ultrasound transmissions/receptions the first set number of times when the first mode is selected, and obtain a second set of reflected waves, for each scanning line, as a result of the executing the set of ultrasound transmissions/receptions the second set number of times when the second mode is selected;

add the first set of reflected waves, for each scanning line, when the first mode is selected, and add the second set of reflected waves, for each scanning line, when the second mode is selected, thereby to cancel a fundamental component included in each reflected wave; and generate a first image of a region by using data obtained by adding the first set of reflected waves when the first mode is selected, and generate a second image of the region by using data obtained by adding the second set of reflected waves when the second mode is selected.

2. The ultrasound diagnosis apparatus according to claim 1, wherein the processing circuitry is further configured to change a gain value used to amplify reflected wave signals received at an amplifier circuit in accordance with a change in a number of sets of ultrasound transmissions/receptions executed by the ultrasound probe.

3. The ultrasound diagnosis apparatus according to claim 2, wherein the processing circuitry is further configured to change the gain value to a smaller value for a larger number of sets of ultrasound transmissions/receptions executed by the ultrasound probe.

4. The ultrasound diagnosis apparatus according to claim 1, wherein
the processing circuitry is further configured to detect a change in a subject region analyzed by using reflected waves or detect motion of the ultrasound probe, and switch the first mode to the second mode based on the change in the subject region or on the motion.

5. The ultrasound diagnosis apparatus according to claim 1, wherein the processing circuitry is further configured to detect motion occurring in a subject region,
determine, based on the motion, a number of sets of ultrasound transmissions/receptions to be executed by the ultrasound probe, and
cause the ultrasound probe to execute an ultrasound transmission/reception in accordance with determined number of sets of ultrasound transmissions/receptions.

6. The ultrasound diagnosis apparatus according to claim wherein the processing circuitry is further configured to detect motion by analyzing reflected waves received through a scan to detect motion, the scan being executed independently of a scan to generate an image, detect motion by analyzing reflected waves received through a scan that has already been executed to generate an image, or detect motion by analyzing, during a scan, reflected waves received in the scan.

7. The ultrasound diagnosis apparatus according to claim 5, wherein the processing circuitry is further configured to detect motion occurring in a subject region, detection being triggered by a change in a certain scan condition, and determine, based on the detected motion, a number of sets of ultrasound transmissions/receptions executed by the ultrasound probe.

8. The ultrasound diagnosis apparatus according to claim 5, wherein the processing circuitry is further configured to store, in a memory, an image generated by the processing circuitry, the storing being triggered by determining that the motion falls below a certain threshold.

9. The ultrasound diagnosis apparatus according to claim 5, wherein the processing circuitry is further configured to display an image generated by the processing circuitry in a paused state, the display being triggered by determining that the motion falls below a certain threshold.

10. The ultrasound diagnosis apparatus according to claim 1,
wherein the processing circuitry is further configured to display, together with the image, information indicating that the second mode is on, when the processing circuitry switches modes to the second mode.

11. The ultrasound diagnosis apparatus according to claim 1, wherein the processing circuitry is further configured to store, in a memory, the image generated by the processing circuitry, which is triggered by switching to the second mode.

12. The ultrasound diagnosis apparatus according to claim 1, wherein the processing circuitry is further configured to display the image generated by the processing circuitry in a paused state, the display being triggered by switching to the second mode.

13. The ultrasound diagnosis apparatus according to claim wherein the processing circuitry is further configured to display an image generated in the first mode and an image generated in the second mode side by side.

14. The ultrasound diagnosis apparatus according to claim 1, wherein the processing circuitry is further configured to switch modes to the second mode in a part of a subject region, and maintain the first mode in the other part of the subject region.

15. The ultrasound diagnosis apparatus according to claim 1, wherein the processing circuitry is further configured to switch between the first mode and the second mode by the direct operation, which is performed through an input interface.

16. The ultrasound diagnosis apparatus according to claim 1, wherein the first set number is one.

* * * * *